(12) United States Patent
Velikyan et al.

(10) Patent No.: US 8,846,001 B2
(45) Date of Patent: Sep. 30, 2014

(54) LABELLED BIOTIN CONJUGATES

(75) Inventors: Irina Velikyan, Uppsala (SE); Elisabeth Blom, Uppsala (SE); Bengt Langstrom, Uppsala (SE)

(73) Assignees: GE Healthcare Limited, Amersham, Buckinghamshire (GB); Hammersmith Imanet Limited, London (GB)

( * ) Notice: Subject to any disclaimer, the term of this patent is extended or adjusted under 35 U.S.C. 154(b) by 116 days.

(21) Appl. No.: 13/395,575

(22) PCT Filed: Sep. 16, 2010

(86) PCT No.: PCT/EP2010/063636
§ 371 (c)(1),
(2), (4) Date: Mar. 12, 2012

(87) PCT Pub. No.: WO2011/033033
PCT Pub. Date: Mar. 24, 2011

(65) Prior Publication Data
US 2012/0177569 A1   Jul. 12, 2012

Related U.S. Application Data

(60) Provisional application No. 61/243,323, filed on Sep. 17, 2009.

(30) Foreign Application Priority Data

Dec. 22, 2009   (GB) ................... 0922369.4

(51) Int. Cl.
*A61K 51/00*   (2006.01)
*A61M 36/14*   (2006.01)

(52) U.S. Cl.
USPC ....................... 424/1.11; 424/1.65

(58) Field of Classification Search
USPC ........................................ 424/1.65
See application file for complete search history.

(56) References Cited

U.S. PATENT DOCUMENTS

| | | | | |
|---|---|---|---|---|
| 5,428,156 A | * | 6/1995 | Mease et al. | 540/474 |
| 5,871,709 A | * | 2/1999 | Gries et al. | 424/1.65 |
| 7,390,828 B2 | * | 6/2008 | Paganelli et al. | 514/387 |

FOREIGN PATENT DOCUMENTS

| | | |
|---|---|---|
| WO | WO 99/30745 | 6/1999 |
| WO | WO 02/066075 | 8/2002 |
| WO | WO 03/014158 | 2/2003 |
| WO | WO 2007/039437 | 4/2007 |

OTHER PUBLICATIONS

Blom, E., et al., Bioconjugate Chemistry, 20:1146-1151 (2009).
Forster, G., et al., The Journal of Nuclear Medicine, 47(1):140-149 (2006).
Hainsworth, J., et al., Bioconjugate Chemistry, 16:1468-1474 (2005).
Lewis, M., et al., Nuclear Medicine and Biology, 29:701-706 (2002).
Sabatino, G., et al., J. Med. Chem., 46:3170-3173 (2003).
Wilbur, D., et al., Bioconjugate Chemistry, 11:569-583 (2000).

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention provides radioactive gallium complexes which comprise DOTA-biotin conjugates, incorporating a linker group. Also described are radiopharmaceutical compositions, and methods and uses of the complexes for in vivo imaging involving pre-targeting with avidin.

7 Claims, 1 Drawing Sheet

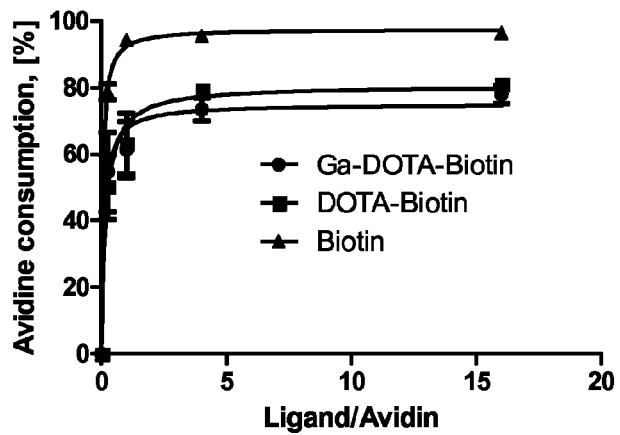
Figure 1. Saturation of the binding of biotin based counterparts (biotin, Compound 5 (DOTA-biotin), and $^{69,71}$Ga-labeled Compound 5 (Ga-DOTA-biotin)) to avidin in solution determined by HPLC analysis.
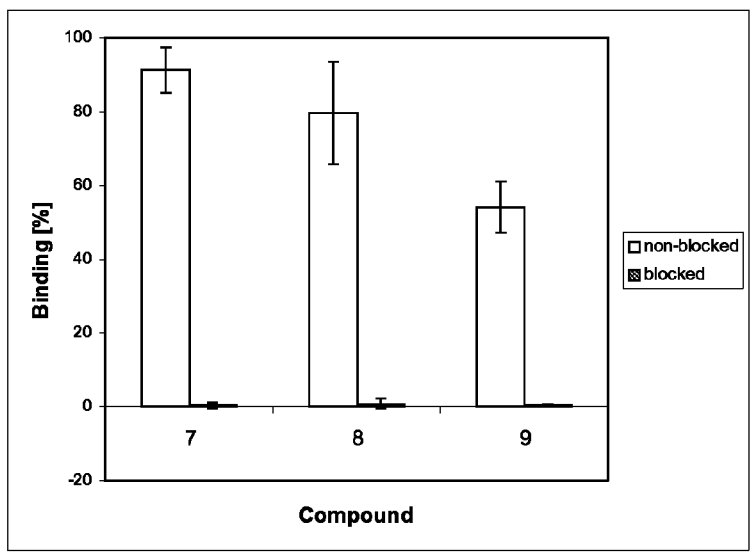
Figure 2. Percent binding for binding of Compounds 7-9 to avidin, blocked and non-blocked. Data are presented as mean ± SD (n = 2).

LABELLED BIOTIN CONJUGATES

This application is a filing under 35 U.S.C. 371 of international application number PCT/EP2010/063636, filed Sep. 16, 2010, which claims priority to Great Britain application number 0922369.4 filed Dec. 22, 2009 and U.S. application No. 61/243,323 filed Sep. 17, 2009.

FIELD OF THE INVENTION

The present invention provides radioactive gallium complexes which comprise DOTA-biotin conjugates, incorporating a linker group. Also described are radiopharmaceutical compositions, and methods and uses of the complexes for in vivo imaging involving pre-targeting with avidin.

BACKGROUND TO THE INVENTION

Biotin possesses an extraordinarily strong binding affinity to avidin and streptavidin ($K_d \approx 10^{-15}$M).(4) The quaternary structure of avidin ($M_w \approx 66$ kDa) consists of a non-covalent tetramer which combine into the active form.(5, 6) Therefore each avidin unit is capable of binding four biotin molecules. (6, 7) This binding property can be utilized in the development of a universal tracer that could be used, for example, in the management of various tumor types (8) based on pretargeting concept as well as in organ transplantation medicine.

In vivo imaging using pre-targeting is a known technique. Thus, biotin-DOTA conjugates [where DOTA is the macrocyclic chelator 2,2',2",2"'-(1,4,7,10-tetraazacyclododecane-1,4,7,10-tetrayl)tetraacetic acid] are described in U.S. Pat. No. 5,608,060. The DOTA-biotin conjugates of U.S. Pat. No. 5,608,060 are as follows:

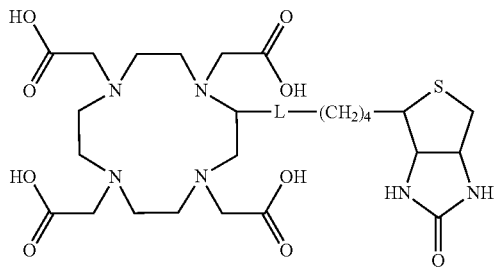

where L is a linker group incorporating a phenylene-$CH_2$— moiety Axworthy et al [Proc. Nat. Acad, Sci. USA, 97(4), 1802-1807 (2000)] disclose pretargeting using avidin-conjugated antibodies and the $^{90}$Y-complex of a DOTA-biotin conjugate for radioimmunotherapy in vivo. The DOTA-biotin conjugate used was that described in U.S. Pat. No. 5,608,060.

WO 02/066075 discloses conjugates of biotin with chelating agents based on functionalisation of biotin with diamines $H_2N-Q-NH_2$, where Q is —$(CH_2)_n$— and n is 4 to 12. The chelator of WO 02/066075 is an N4 macrocycle, of variable ring size, which may be attached at several locations. WO 02/066075 also discloses radiometal complexes of the conjugates, with $^{25}$Fe, $^{52m}$Mn, $^{55}$Co, $^{64}$Cu, $^{67}$Ga, $^{68}$Ga, $^{99m}$Tc, $^{111}$In, $^{123}$I, $^{125}$I, $^{131}$I, $^{32}$P, $^{47}$Sc, $^{67}$Cu, $^{90}$Y, $^{109}$Pd, $^{111}$Ag, $^{149}$Pm, $^{186}$Re, $^{188}$Re, $^{211}$At, $^{212}$Bi, $^{213}$Bi, $^{105}$Rh, $^{153}$Sm, $^{177}$Lu and $^{198}$Au. The only specific complex exemplified by WO 02/066075 is with $^{90}$Y.

Lewis et al [Nucl. Med. Biol., 29, 701-706 (2002)] disclose the preparation of a $^{66}$Ga complex of the DOTA-biotin conjugate of U.S. Pat. No. 5,608,060. The main focus of Lewis et al was on the feasibility of obtaining $^{66}$Ga in sufficient purity for radiopharmaceutical applications, rather than applications of the labelled DOTA conjugate.

Hainsworth et al [Bioconj. Chem., 16(6), 1468-1474 (2005)] disclose DOTA-biotin conjugates having amide or amine linkages in the linker group between the DOTA chelator and the biotin.

Forster et al [J. Nucl. Med., 47(1), 140-149 (2006)] investigate methods of reducing the renal radiation dose in radio-immunotherapy. They used DOTA-biotin conjugates labelled with $^{67}$Ga as a model system. The DOTA-biotin conjugate used was that of Axworthy et al (above), i.e. that of U.S. Pat. No. 5,608,060.

Blom et al [Bioconj. Chem., 20(6), 1146-1151 (2009)] disclose the $^{68}$Ga-labelling of DOTA-biotin conjugates where the effect of the linker group between the DOTA and the biotin is studied.

There is still a need for alternative and/or improved radiotracers and radiopharmaceuticals suitable for pre-targeting imaging using the biotin/avidin system in vivo.

THE PRESENT INVENTION

The present invention provides radioactive gallium complexes which comprise a DOTA-biotin conjugate, having various alkyl or polyethylene glycol (PEG) linker groups. The different linkers between the biotin and the DOTA chelator were used to explore the effect of lipophilicity on the binding of the conjugate to avidin. $^{68}$Ga-radiolabelling was successfully performed. The labeling chemistry is straightforward and site-specific.

Binding of the labeled and non-labeled conjugates to avidin in solution compared to the binding of native biotin. It was shown that all counterparts maintained their affinity to avidin. The binding of the labeled compounds to avidin was 54-91% within 5 min. Blocking experiments confirmed the specificity of the binding of the biotin analogues to avidin.

The present invention provides gallium radiometal complexes which permit the prolongation of the physiological half-life of the biotin tracer, eg, by the introduction of polyethylene glycol (PEG) linkers. The gallium-based complexes of the invention permit the further optimisation of pretargeting imaging in vivo.

One possible such application is to monitor the survival of transplanted avidin-coated islets of Langerhans in pancreas, in connection with the development of islet transplantation methods. Thus, the transplantation of donor pancreas isolated islets into a patient with type I diabetes for therapeutic purposes has been studied for decades. However, obstacles like low graft survival and islet rejection preclude its widespread application.(1) The understanding of the underlying mechanisms and the monitoring of the procedure in vivo would contribute considerably into development of the field. A noninvasive imaging technique such as Positron Emission Tomography (PET) with good resolution, high sensitivity and accurate quantification could provide a clinical tool to evaluate and monitor the graft survival during islet transplantation and also to optimise the latter.(2) The biotin based tracer would possess advantages over [$^{18}$F]FDG(9, 10) in terms of binding specificity, higher accumulation and longer residence. For example, in porcine islets in vitro the retention of [$^{18}$F]FDG had a half-life of 141.5 min.(9)

BRIEF DESCRIPTION OF THE DRAWINGS

FIG. 1 shows the saturation of the binding of biotin based counterparts (biotin, Compound 5 (DOTA-biotin), and $^{69,71}$Ga-labeled Compound 5 (Ga-DOTA-biotin)) to avidin in solution determined by HPLC analysis.

FIG. 2 shows the percent binding for binding of Compounds 7-9 to avidin, blocked and non-blocked. Data are presented as mean ±SD (n=2).

DETAILED DESCRIPTION OF THE INVENTION

In a first aspect, the present invention provides a radioactive gallium complex which comprises a metal complex of a radioisotope of gallium with a DOTA-biotin conjugate of Formula (I):

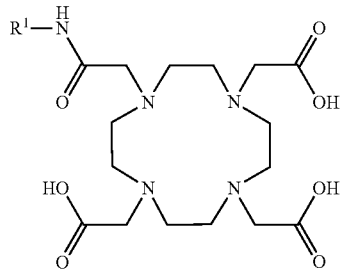

where:
R[1] is biotin-NH-L[1]-;
L[1] is a linker group of formula —(CH$_2$)$_n$— or is L$^{PEG}$,
wherein L$^{PEG}$ is —(CH$_2$)$_2$[OCH$_2$CH$_2$O]$_m$—(CH$_2$)$_2$—;
wherein n is an integer of value 3 to 6, and m is an integer of value 1 to 10.

By the term "metal complex" is meant a coordination complex of the radioactive gallium with the DOTA ligand. Preferably, such complexes comprises gallium in the Ga(III) oxidation state. Such gallium-DOTA complexes are known in the art.

The abbreviation DOTA has its conventional meaning, and corresponds to: 2,2',2'',2'''-(1,4,7,10-tetraazacyclododecane-1,4,7,10-tetrayl)tetraacetic acid.

The term "biotin" has its conventional meaning. The formula biotin-NH-L[1]- denotes that the free carboxybutyl group of biotin is conjugated via an amide bond to L[1]. Biotin (5-[(3aS,4S,6aR)-2-oxohexahydro-1H-thieno[3,4-d]imidazol-4-yl]pentanoic acid) is a naturally occurring vitamin, which is generally found in its protein bound form. It acts as a carboxyl carrier in four carboxylase enzymes in animals and is important in lipid, glucose, energy and amino acid metabolism.(3)

Preferred Aspects.

In Formula (I), L[1] is preferably L$^{PEG}$. m is preferably 1 to 6, more preferably 1 to 4.

The radioisotope of gallium is preferably suitable for PET or SPECT radioisotope imaging in vivo. Preferred such isotopes for PET imaging are $^{66}$Ga or $^{68}$Ga. A preferred such isotope for SPECT imaging is $^{67}$Ga. The radioisotope of gallium is most preferably $^{68}$Ga. Thus $^{68}$Ga (t$_{1/2}$=68 min; 90% β$^+$-emission), is available from a commercial long shelf-life generator with parent radionuclide $^{68}$Ge with a half-life of 270 days. The half-life of $^{68}$Ga permits production and utilization of $^{68}$Ga-based radiopharmaceuticals, but at the same time it avoids unnecessary patient irradiation allowing ambulatory examinations. The resulting $^{68}$Ga PET-images are of good quality and allow quantification.

The conjugate of the first aspect is preferably of Formula (II):

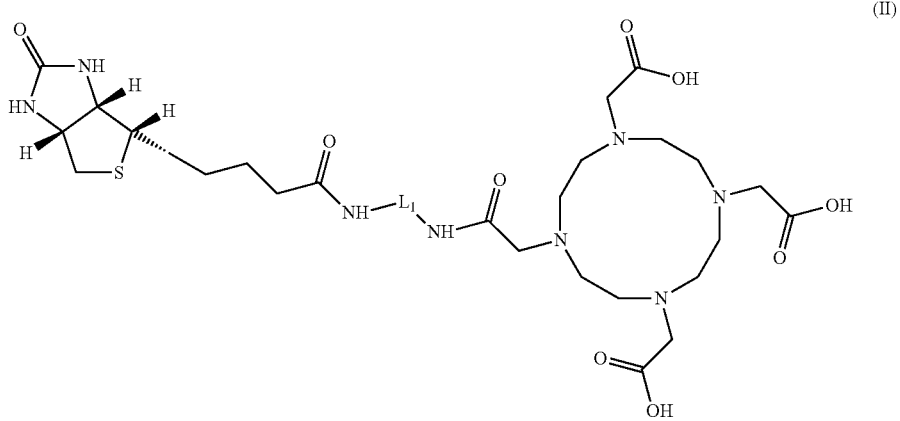

In Formula (II), preferred L[1] groups are as defined for Formula (I).

The gallium complexes of the first aspect are prepared by labelling the conjugate of Formula (I) with Ga(III) cation using a solution in hydrochloric acid of the radiometal. In the case of $^{68}$Ga, is eluted from the $^{68}$Ge/$^{68}$Ga generator system and 2-[4-(2-hydroxyethyl)piperazin-1-yl]ethanesulfonic acid (HEPES) as a buffer, as shown in Scheme 1 (below). This buffer is biocompatible and does not need to be removed prior to biological studies. The labeling reaction was performed at pH 4.6-5.0 at room temperature or by using conventional or microwave heating. By using conventional or microwave heating at 90° C. the incorporation of $^{68}$Ga(III) is 90% within 5 or 2 min respectively. When the labeling was performed at room temperature, however, at least 90 min reaction time was required to reach 90% incorporation, as discussed below. The synthesis of the $^{68}$Ga-labeled compound can be accomplished within less than 30 min starting from the elution from the generator to the HPLC analysis, when heating is applied in the reaction and when the incorporation exceeds 90% no purification is necessary. Due to the short time of synthesis little activity is lost, allowing for imaging studies within the following 2-3 hours.

Scheme 1.

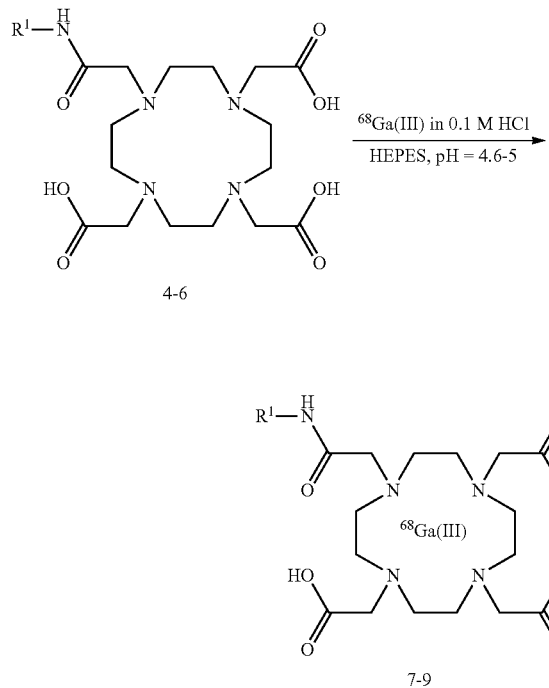

Compounds 4 and 7, R¹ = biotin-NH—(CH₂)₅—

Compounds 5 and 8, R¹ = biotin-NH—(CH₂)₂—O—(CH₂)₂—O—(CH₂)₂—

Compounds 6 and 9, R¹ = biotin-NH—(CH₂)₂—O—(CH₂)₂—O—(CH₂)₂—O—(CH₂)₂—

In a second aspect, the present invention provides a radiopharmaceutical composition which comprises the radioactive gallium complex of the first aspect, together with a biocompatible carrier medium.

Preferred aspects of the radioactive gallium complex in the second aspect are as described for the first aspect (above).

The "biocompatible carrier medium" is a fluid, especially a liquid, in which the gallium radiometal complex is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. As indicated above, the pH of the biocompatible carrier medium for intravenous injection is suitably in the range 4.0 to 10.5.

In a third aspect, the present invention provides a DOTA-biotin conjugate of Formula (I) useful in the preparation of the radioactive gallium complex of the first aspect, or the radiopharmaceutical composition of the second aspect, wherein said conjugate is as defined in the first aspect. Preferred aspects of the DOTA-biotin conjugate of Formula (I) in the third aspect are as described for the first aspect (above).

The conjugates of Formula (I) can be prepared as described in Scheme 2:

Scheme 2.

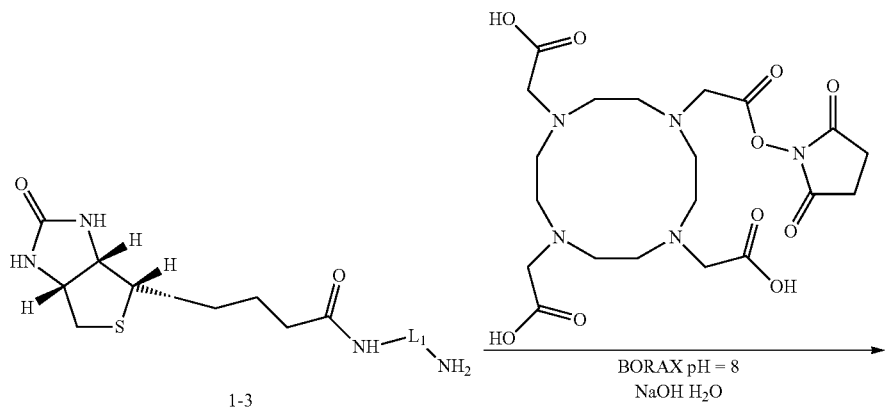

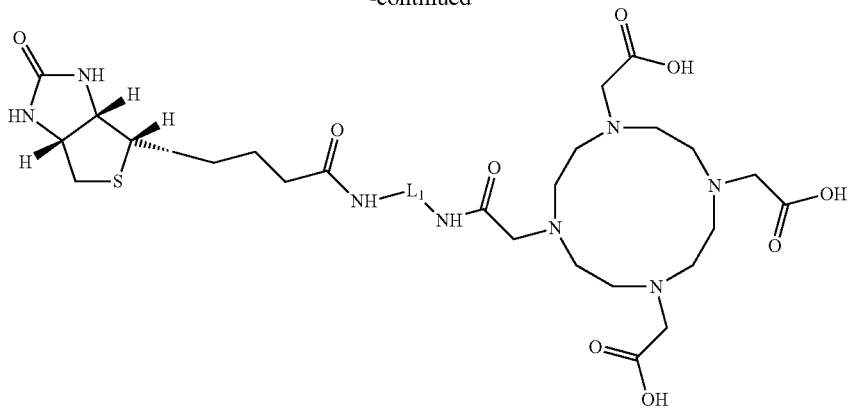

4-6

Compound 1 and Compound 4, $L^1 =$ —$(CH_2)_5$—

Compound 2 and Compound 5, $L^1 =$ —$(CH_2)_2$—O—$(CH_2)_2$—O—$(CH_2)_2$—

Compound 3 and Compound 6, $L^1 =$ —$(CH_2)_2$—O—$(CH_2)_2$—O—$(CH_2)_2$—O—$(CH_2)_2$— .

In Scheme 2, amine-functionalised biotins (Compounds 1 to 3) are reacted with DOTA-NHS ester to gives the desired conjugates (Compounds 3 to 6). Further details are provided in Examples 1 to 3 (below).

In a fourth aspect, the present invention provides a method of diagnostic imaging in vivo of a mammalian subject, wherein said method comprises:
  (i) provision of a mammalian subject to which an avidin-conjugated biological targeting molecule has been previously administered and allowed to localise at a binding site of said biological targeting molecule within said subject;
  (ii) administration of a biotin pre-targeting agent which comprises the radioactive gallium complex of the first aspect, or the radiopharmaceutical composition of the second aspect;
  (iii) waiting a suitable time until the administered pre-targeting agent of step (ii) has bound to the localised biological targeting molecule of step (i) via avidin-biotin binding to give the biotin pre-targeting agent localised at the binding site of step (i);
  (iv) imaging the subject using the radioactive emissions from the localised biotin pre-targeting agent of step (iii).

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

In a fifth aspect, the present invention provides a method of diagnosis of the mammalian body, which comprise the method of diagnostic imaging of the fourth aspect.

The invention is illustrated by the following Examples. Examples 1 to 3 provide the syntheses of the conjugates Compounds 4 to 6 respectively. The biotin-DOTA conjugates (Compounds 4 to 6) were prepared by reacting DOTA-NHS-ester (where NHS=N-hydroxysuccinimide) with the corresponding biotin-amines (Compounds 1 to 3) in water at pH 7-8 using a mixture of sodium tetraborate decahydrate (Borax) and sodium hydroxide as buffer (Scheme 2). The yield of the product after purification by semi-preparative HPLC was 34-47%. When the reaction was conducted at pH 4 in the synthesis of Compound 5, using sodium dihydrogen phosphate and no added sodium hydroxide as buffer, the yield was only 7%.

Example 4 provides the use of HPLC to estimate the relative lipophilicity of the biotin conjugates and corresponding gallium complexes of the invention. Adding DOTA to the biotin amines makes them more lipophilic, even though DOTA itself is a very hydrophilic molecule. When a gallium (III) ion coordinated to the conjugate, the lipophilicity increases, as can be seen from the retention times on the analytical HPLC column for Compounds 4-9 shown in Table 1. That is believed to be due to a change in geometry of the DOTA chelator is changed. For example in Ga-DOTA-D-PHENH$_2$ the chelator gets a cis-pseudo-octahedral geometry when the gallium(III) ion is introduced.(13)

Example 5 provides the $^{68}$Ga-labelling of the conjugates. The $^{68}$Ga(III) is eluted from the $^{68}$Ge/$^{68}$Ga generator by using 6 mL of a solution of hydrochloric acid. This makes the specific activity rather low, but it can be raised by pre-concentration using an anion exchange column.(11) The volume can reduced to 200 μL and the resulting $^{68}$Ga(III) solution successfully used in labeling experiments. The specific activity can be raised by approximately a factor of 4.

Example 6 provides the synthesis of non-radioactive gallium complex, used for reference in the avidin binding assay of Example 7. Stable gallium isotope ($^{69,71}$Ga) was introduced to the biotin-DOTA conjugates by using a water solution of GaCl$_3$ at 90° C. for 5 min and the reaction conditions in Scheme 1. The masses of the gallium-conjugates were determined by LC-MS. The stable gallium labeled conjugates were added as reference compounds in the LC-runs of labeling reactions for identification of the $^{68}$Ga-labeled compounds.

Example 7 provides the avidin binding of both the unlabelled conjugates and their corresponding gallium complexes, compared to biotin itself. All ligands (Compounds 4-9) retained their capacity to bind to the avidin in solution. As an example the results of the saturation experiments with the biotin counterparts native biotin; DOTA-biotin (Compound 5) and Ga-DOTA-biotin ($^{69,71}$Ga—Compound 5) on avidin are shown in FIG. 1. Native biotin showed the highest binding and the analogues Compound 4 and 5 reached saturation at approximately 15% below biotin. Compound 6, with the longer PEG-linker, had the lowest binding, saturation was reached approximately 40% below biotin. In all cases the binding was somewhat lower when $^{69,71}$Ga was inserted into the DOTA chelator and the molecule became neutral. Without the gallium ion, the molecule has a three minus charge. Increasing the incubation time to 40 min did not increase the binding of any of the analogues.

Approximately 80-90% of the labeled compounds (Compounds 7 and 8) were bound to avidin within 5 min, but only 50% of Compound 9. This lower binding of Compound 9 was also seen from the saturation experiments with avidin discussed previously. The pegylation, which also increases the size of the molecule, especially in the case of Compound 9 leads to lower binding. In order to demonstrate that the binding was receptor-specific, a 50-fold excess of native biotin was first added to avidin solutions in the control experiments and incubated at room temperature for 10 min, in order to saturate the binding sites of the avidin. Thereafter an equimolar amount of the labeled Compounds (Compounds 7-9) was added and incubated together with the blocked avidin for 5 min. HPLC analysis showed approximately 0.5-1.5% binding of the $^{68}$Ga-labeled compounds to the blocked avidin. Results of the binding specificity experiments demonstrated that the binding was site-specific, since it could be precluded by pre-saturation of avidin with native ligand, biotin.

This demonstrates that the modifications maintain the avidin-binding properties, and that the binding of the conjugate should be sufficient to be used for its purpose in labeling of avidin treated islets of Langerhans.

EXPERIMENTAL PROCEDURES

Materials

N-(5-Aminopentyl)-5-[(3aS,4S,6aR)-2-oxohexahydro-1H-thieno[3,4-d]imidazol-4-yl]pentanamide, N-{2-[2-(2-aminoethoxy)ethoxy]ethyl}-5-[(3aS,4S,6aR)-2-oxohexahydro-1H-thieno[3,4-d]imidazol-4-yl]pentanamide, N-(2-{2-[2-(2-aminoethoxy)ethoxy]ethoxy}ethyl)-5-[(3aS,4S,6aR)-2-oxohexahydro-1H-thieno[3,4-d]imidazol-4-yl] pentanamide was obtained from Pierce Biotechnology, Inc. (Rockford, USA) and (+)-biotin from Alfa Aesar, Chemtronica. 2,2',2''-(10-{2-[(2,5-Dioxopyrrolidin-1-yl) oxy]-2-oxoethyl}-1,4,7,10-tetraazacyclododecane-1,4,7-triyl)triacetic acid HPF$_6$.TFA (DOTA-NHS-ester) from Macrocyclics (Dallas, USA). 2-[4-(2-Hydroxyethyl)piperazin-1-yl]ethanesulfonic acid (HEPES), trifluoroacetic acid (TFA), double distilled hydrochloric acid (Riedel de Haën), avidin (lyophilised powder, from egg white), sodium tetraborate decahydrate (Borax) and gallium (III) chloride were obtained from Sigma-Aldrich. Sodium dihydrogen phosphate was obtained from Merck euro lab. The purchased chemicals were used without further purification.

Analytical Methods.

HPLC analyses of radiolabelled compounds were performed on a Beckman Nouveau HPLC system equipped with a Beckman 166 variable-wavelength UV detector and a β$^+$-flow detector, using a isocratic elution with water (A) (92%) and acetonitrile (B) (8%), both containing 0.05% TFA, as mobile phase with UV detection at 223 nm. For analytical HPLC a Grace Vydac C18 Protein and Peptide column (150× 4.6, 5µ) was used, flow 1 mL/min. For semi-preparative HPLC a Grace Vydac C18 Protein and Peptide column (150× 10, 10µ) 300 Å TP silica, on a Gilson HPLC system was used, flow 5 mL/min, (8% (B)). Millipore water (18 mΩ from Purelab Maxima Elga system (Bucks, UK) was used throughout the synthesis. NMR spectra were recorded with a Varian Unity spectrometer at 400 MHz for $^1$H and at 100 MHz for $^{13}$C, at 25° C. in CD$_3$OD (solvent peak used as reference). LC-MS analysis was performed using a Micromass VG Quattro mass spectrometer with electrospray ionization. The same analytical HPLC column and mobile phases were used at a flow of 0.3 mL/min. The radioactivity was measured in an ion chamber, Veenstra Instrumenten by, VDC-202.

Microwave Heating.

Microwave heating was performed in a SmithCreator™ monomodal cavity (Biotage AB, Uppsala, Sweden) using a 200-1000 µL Smith Process Vial™ microwave vial.

Example 1

Synthesis of Compound 4

Compound 1 (0.015 g, 46 µmol) was dissolved in 250 µL aqueous Borax (0.08 M, pH 9.3). The solution was cooled to 0° C. and DOTA-NHS ester (0.057 g, 69 µmol) was added and the resulting pH was 2. The pH was raised to 7 by adding 200 µL of a 1:1 v/v mixture of 1M NaOH (aq) and Borax (aq). The temperature was raised to room temperature and stirred for 24 h. The reaction mixture was purified by semi-preparative HPLC (6% (B) isocratic) giving the desired product as a colourless oil (0.011, 34% yield). $^1$H NMR (400 MHz, CD$_3$OD, 25° C.): δ=4.51 (dd, J=5.1, 7.9 Hz, 1H), 4.31 (dd, J=4.6, 7.9 Hz, 1H), 3.98 (m, 4H), 3.83 (m, 12H), 3.25-3.16 (m, 13H), 2.94 (dd, J=4.9, 12.6 Hz, 1H), 2.73 (d, J=12.6 Hz, 1H), 2.21 (t, J=7.2 Hz, 2H), 1.80-1.27 (m, 12H). $^{13}$C NMR (100 MHz, CD$_3$OD, 25° C.): δ=176.0, 165.8, 162.9, 162.0, 63.4, 61.7, 57.0, 54.6, 51.6, 51.1, 50.7, 41.0, 40.5, 40.2, 36.8, 30.1, 29.9, 29.7, 29.5, 26.9, 25.2. ESI-MS: m/z 715 [M+H]$^+$, 358 [M+2H]$^{2+}$.

Example 2

Synthesis of Compound 5

Compound 2 (0.011 g, 29 µmol) was dissolved in 250 µL aqueous Borax (0.08 M, pH 9.3) (or 250 µL aqueous sodium dihydrogen phosphate(12) (0.2 M, pH 8.5). The solution was cooled to 0° C. and DOTA-NHS ester (0.030 g, 36 µmol) was added and the resulting pH was 4. The pH was raised to 8 by adding 100 µL of a 1:5 v/v mixture of 1M NaOH (aq) and Borax (aq). The temperature was raised to room temperature and stirred for 24 h. The reaction mixture was purified by semi-preparative HPLC (6% (B) isocratic) giving the desired product as a colorless oil (0.010, 47% yield). $^1$H NMR (400 MHz, CD$_3$OD, 25° C.): δ=4.50 (dd, J=5.0, 8.0 Hz, 1H), 4.31 (dd, J=4.5, 8.0 Hz, 1H), 3.92 (m, 4H), 3.83 (m, 12H), 3.64-3.62 (m, 4H), 3.60-3.54 (m, 6H), 3.41 (t, J=5.4 Hz, 2H), 3.39-3.33 (m, 8H), 3.25-3.19 (m, 1H), 2.94 (dd, J=5.0, 12.8 Hz, 1H), 2.72 (d, J=12.8 Hz, 1H), 2.23 (t, J=7.5 Hz, 2H), 1.81-1.54 (m, 4H), 1.50-1.41 (m, 2H). $^{13}$C NMR (100 MHz, CD$_3$OD, 25° C.): δ=176.3, 166.1, 163.3, 162.5, 71.3, 71.2, 70.6, 70.4, 63.4, 61.7, 57.0, 51.9, 49.8, 41.0, 40.4, 40.3, 36.8, 29.7, 29.5, 26.8. ESI-MS: m/z 761 [M+H]$^+$, 381 [M+2H]$^{2+}$.

Example 3

Synthesis of Compound 6

Compound 3 (0.017 g, 40 µmol) was dissolved in 250 µL aqueous Borax (0.08 M, pH 9.3). The solution was cooled to 0° C. and DOTA-NHS ester (0.050 g, 60 µmol) was added and the resulting pH was 2. The pH was raised to 7 by adding 200 µL of a 1:1 v/v mixture of 1M NaOH (aq) and Borax (aq). The temperature was raised to room temperature and stirred for 24 h. The reaction mixture was purified by semi-preparative HPLC (8% (B) isocratic) giving the desired product as a colourless oil (0.012, 37% yield). $^1$H NMR (400 MHz, CD$_3$OD, 25° C.): δ=4.50 (dd, J=4.9, 7.9 Hz, 1H), 4.31 (dd, J=4.5, 7.9 Hz, 1H), 3.93 (m, 4H), 3.83 (m, 12H), 3.68-3.61 (m, 10H), 3.60-3.53 (m, 4H), 3.41 (t, J=5.3 Hz, 2H), 3.35-3.30 (m, 8H), 3.25-3.18 (m, 1H), 2.94 (dd, J=5.0, 12.8 Hz, 1H), 2.72 (d, J=12.8 Hz, 1H), 2.22 (t, J=7.4 Hz, 2H), 1.80-1.54 (m, 4H), 1.51-1.40 (m, 2H). $^{13}$C NMR (100 MHz, CD$_3$OD, 25° C.): δ=176.2, 166.1, 163.0, 162.7, 71.6, 71.5, 71.2, 71.1, 70.5, 70.4, 63.4, 61.7, 57.1, 41.1, 40.4, 40.3, 36.7, 31.6, 29.8, 29.6, 26.9. ESI-MS: m/z 806 [M+H]$^+$, 404 [M+2H]$^{2+}$.

Example 4

Lipophilicity of Compounds 4 to 9

According to the retention times on the analytical HPLC column shown in Table 1, the lipophilicity of the three synthesised conjugates increases in the order Compound 5<Compound 4<Compound 6.

TABLE 1

Retention times on analytical HPLC for Compounds 4-9.

| Compound | Retention time$^a$ (min) | Retention time$^b$ (min) |
|---|---|---|
| 4 | 6.9 | 9.4 |
| 5 | 6.1 | 7.3 |
| 6 | 9.5 | 12.4 |

$^a$Retention time on analytical HPLC column.
$^b$Retention time for respective $^{68}$Ga-labeled compound (Compounds 7 to 9) on analytical HPLC column.

Example 5

$^{68}$Ga Radiolabelling of Compounds 4 to 6

Preparation of $^{68}$Ga.
$^{68}$Ga (T$_{1/2}$=68 min, β$^+$=89% and EC=11%) was available from a $^{68}$Ge/$^{68}$Ga generator system (Cyclotron Co., Ltd, Obinsk, Russia) where $^{68}$Ge (T$_{1/2}$=270.8 d) was attached to a column of an inorganic matrix based on titanium dioxide. The initial $^{68}$Ge activity loaded onto the generator column was 1850 MBq. The specified shelf life of the generator was 2-3 years. The $^{68}$Ga was eluted with 6 mL of 0.1 M hydrochloric acid.
Preconcentration Procedure.
(11) The $^{68}$Ge/$^{68}$Ga generator was eluted with 6 mL of a 0.1 M HCl (aq) solution. To this eluate solution was 5 mL of 30% HCl additionally added. The resulting solution was passed through an anion exchange column (Chromafix 30-PS—HCO$_3$, Macharey-Nagel (Germany) at a flow rate of 4 mL/min. Thereafter the $^{68}$Ga ions were eluted with deionized water (4×50 µL) at a flow rate of 0.5 mL/min. The final solution was used for labeling reactions.
General Labeling Procedure.
HEPES (0.048 g, 0.20 mmol) was dissolved in 200 µL of $^{68}$Ga eluate [in 0.1 M HCl (aq)] in a 2 mL Eppendorf tube. Thereafter the biotin-DOTA conjugate (Compounds 4 to 6; 1-70 nmol), in water solution, was added, and the total volume was adjusted to 280 µL by addition of water. The pH was adjusted to 4.6-5 by adding 2M NaOH (aq), if necessary. The reaction took place at room temperature or by using conventional heating at 90° C. for 5 min or microwave heating at 90° C. for 2 min.
The incorporation of $^{68}$Ga(III) using 1-20 nmol of Compounds 4-6 at 90° C. by conventional heating for 5 min was investigated. A plateau of 95% incorporation was reached at 10 nmol using the described setup. This amount (10 nmol) was thereafter used in the subsequent labeling reactions.
Incorporation of $^{68}$Ga(III) at room temperature, at different time points, was explored using 10 nmol of Compound 5. It was concluded from these experiments that it is not reasonable to do the labeling reaction at ambient temperature since it will take at least 90 min to reach 90% incorporation, and after this time the radioactivity has decreased by a factor of almost 1.5.

Example 6

Synthesis of $^{69,71}$Ga-Reference Compounds

HEPES (0.048 g, 0.20 mmol) was dissolved in 200 µL of $^{68}$Ga eluate and pH was adjusted to 4.6-5 by adding 2M NaOH (aq). Thereafter the respective precursor (Compounds 4 to 6; 70 nmol), and $^{69,71}$GaCl$_3$ (56 mM, 2 µL, 112 nmol) in water solution, were added. The reaction mixture was heated at 90° C. for 5 min.
ESI-MS: $^{69,71}$Ga-4 m/z 784 [M+H]$^+$, 393 [M+2H]$^{2+}$, $^{69,71}$Ga-5 m/z 827 [M+H]$^+$, 414 [M+2H]$^{2+}$, $^{69,71}$Ga-6 m/z 874 [M+H]$^+$, 438 [M+2H]$^{2+}$.

Example 7

Avidin Binding Reactions

Various amounts of biotin, Compounds 4-6 or $^{69,71}$Ga-biotin Compounds 4-6 (2-128 nmol) were incubated with a constant amount of avidin (2 nmol) for 5 min at room temperature in water (150 µL total volume). The percentage binding was determined by HPLC analysis. HPLC program: 8% (B) for 12 min, then up to 80% in 10 min for Compounds 4 and 5, 8% (B) for 15 min, then up to 80% in 18 min for Compound 6. Labeled Compounds 7 to 9, were incubated with avidin for 5 min at room temperature and analyzed by the same HPLC programs.
Blocking Experiment.
Avidin (2 nmol) was incubated together with biotin (400 nmol) in water (100 µL) for 10 min. HPLC analysis confirmed the blocking. Thereafter one of Compounds 7-9 (8 nmol) was added in each experiment and incubated together with the blocked avidin for 5 min (total volume 360 µL) and the solution was again analyzed by HPLC. HPLC program: 8% (B) for 12 min, then up to 80% in 10 min for Compounds 7 and 8, 8% (B) for 15 min, then up to 80% in 18 min for Compound 9.
The incubation was carried out during 5 min at room temperature with varied ligand concentration resulting in ligand/avidin ratio of 0.25, 1, 4 and 16. The results are shown in FIG. 1. Data are presented as mean±SD (n=2). Various amounts of the biotin or its analogues (2-128 nmol) were incubated together with a constant amount of avidin (2 nmol), at room temperature for 5 min. The binding experiments were carried out both in water and HEPES buffer solutions and it was shown that the buffer did not affect the binding. The specific binding presented as the avidin consumption in percentage was plotted against the ratio of total molar concentration of added ligands and avidin. The result was analyzed by nonlinear regression using the GraphPad Prism Software. All the curves reached a maximum value, indicating saturation and close affinity values.

Binding of the $^{68}$Ga-labeled conjugates to avidin was studied using HPLC, using equimolar amounts of the conjugate and the protein (67 mM). The biotin analogues labeled with [68]Ga(III) were incubated with avidin at room temperature. The results are shown in FIG. 2.

REFERENCES (1) Shapiro, A. M. J., Lakey, J. R. T., Ryan, E. A., Korbutt, G. S., Toth, E., Warnock, G. L., Kneteman, N. M., and Rajotte, R. V. (2000) Islet transplantation in seven patients with type 1 diabetes mellitus using a glucocorticoid-free immunosuppressive regimen. *N. Engl. J. Med.* 343, 230-238.
(2) Paty, B. W., Bonner-Weir, S., Laughlin, M. R., McEwan, A. J., and Shapiro, A. M. J. (2004) Toward development of imaging modalities for islets after transplantation: insights from the National Institutes of Health Workshop on Beta Cell Imaging. *Transplantation.* 77, 1133-1137.
(3) Combs, G. F. Jr. (1992) *The Vitamins: Fundamental Aspects of Nutrition and Health*, Academic Press Inc, San Diego, pp 336.
(4) Bayer, E. A., and Wilchek, M. (1980) The use of the avidin-biotin complex as a tool in molecular biology. *Methods Biochem. Anal.* 26, 1-45.
(5) DeLange, R. J., and Huang, T.-S. (1971) Egg white avidin. III. Sequence of the 78-residue middle cyanogen bromide peptide. Complete amino acid sequence of the protein subunit. *J. Biol. Chem.* 246, 698-709.
(6) Green, N. M. (1975) Avidin. *Adv. Protein Chem.* 29, 85-133.
(7) Livnah, O., Bayer, E. A., Wilchek, M., and Sussman, J. L. (1993) Three-dimensional structures of avidin and the avidin-biotin complex. *Proc. Natl. Acad. Sci. USA.* 90, 5076-5080.
(8) Sabatino, G., Chinol, M., Paganelli, G., Papi, S., Chelli, M., Leone, G., Papini, A. M., De Luca, A., and Ginanneschi, M. (2003) A new biotin derivative-DOTA conjugate as a candidate for pretargeted diagnosis and therapy of tumors. *J. Med. Chem.* 46, 3170-3173.
(9) Eich, T., Eriksson, O., Sundin, A., Estrada, S., Brandhorst, D., Brandhorst, H., Langstrom, B., Nilsson, B., Korsgren, O., and Lundgren, T. (2007) Positron emission tomography: a real-time tool to quantify early islet engraftment in a preclinical large animal model. *Transplantation.* 84, 893-898.
(10) Toso, C., Zaidi, H., Morel, P., Armanet, M., Andres, A., Pernin, N., Baertschiger, R., Slosman, D., Buhler, L. H., Bosco, D., and Berney, T. (2005) Positron-emission tomography imaging of early events after transplantation of islets of Langerhans. *Transplantation.* 79, 353-355.
(11) Velikyan, I., Beyer, G. J., and Langstrom, B. (2004) Microwave-supported preparation of (68)Ga bioconjugates with high specific radioactivity. *Bioconjugate Chem.* 15, 554-560.
(12) Cauchon, N., Langlois, R., Rousseau, J. A., Tessier, G., Cadorette, J., Lecomte, R., Hunting, D. J., Pavan, R. A., Zeisler, S. K., and van Lier, J. E. (2007) PET imaging of apoptosis with (64)Cu-labeled streptavidin following pretargeting of phosphatidylserine with biotinylated annexin-V. *Eur. J. Nucl. Med. Mol. Imaging.* 34, 247-258.
(13) Heppeler, A., Froidevaux, S., Mäcke, H. R., Jermann, E., Béhé, M., Powell, P., and Hennig, M. (1999) Radiometal-Labelled Macrocyclic Chelator-Derivatised Somatostatin Analogue with Superb Tumour-Targeting Properties and Potential for Receptor-Mediated Internal Radiotherapy. *Chem. Eur. J.* 5, 1974-1981.

What is claimed is:

1. A radioactive gallium complex which comprises a metal complex of a radioisotope of gallium with a DOTA-biotin conjugate of Formula (I):

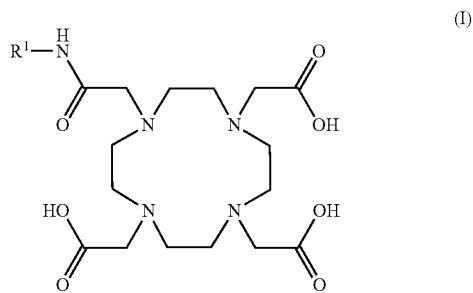

where:
$R^1$ is biotin-NH-$L^1$-;
$L^1$ is a linker group of formula $L^{PEG}$,
wherein $L^{PEG}$ is —$(CH_2)_2[OCH_2CH_2O]_m$—$(CH_2)_2$—;
wherein m is an integer of value 1 to 4.

2. The radioactive gallium complex of claim 1, where the radioisotope of gallium is [66]Ga, $^{67}$Ga or [68]Ga.

3. The radioactive gallium complex of claim 2, where the radioisotope of gallium is [68]Ga.

4. The radioactive gallium complex of claim 1, where the conjugate is of Formula (II):

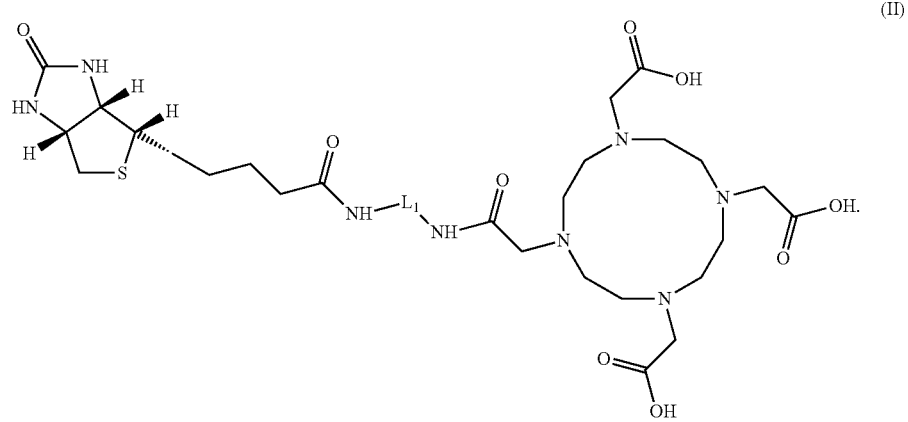

5. A radiopharmaceutical composition which comprises the radioactive gallium complex of claim 1, together with a biocompatible carrier medium.

6. A DOTA-biotin conjugate of Formula (I) useful in the preparation of the radioactive gallium complex of claim 1, wherein said conjugate is as defined in claim 1.

7. A method of diagnostic imaging in vivo of a mammalian subject, wherein said method comprises:
  (i) provision of a mammalian subject to which an avidin-conjugated biological targeting molecule has been previously administered and allowed to localise at a binding site of said biological targeting molecule within said subject;
  (ii) administration of a biotin pre-targeting agent which comprises the radiopharmaceutical composition of claim 5;
  (iii) waiting a suitable time until the administered pre-targeting agent of step (ii) has bound to the localised biological targeting molecule of step (i) via avidin-biotin binding to give the biotin pre-targeting agent localised at the binding site of step (i);
  (iv) imaging the subject using the radioactive emissions from the localised biotin pre-targeting agent of step (iii).

* * * * *